(12) United States Patent
Coley et al.

(10) Patent No.: US 8,716,518 B2
(45) Date of Patent: May 6, 2014

(54) PHOTOACID GENERATING MONOMER AND PRECURSOR THEREOF

(75) Inventors: Suzanne M. Coley, Mansfield, MA (US); David R. Wilson, Midland, MI (US); Francis J. Timmers, Midland, MI (US)

(73) Assignees: Rohm and Haas Electronic Materials LLC, Marlborough, MA (US); Dow Global Technologies LLC, Midland, MI (US)

( * ) Notice: Subject to any disclaimer, the term of this patent is extended or adjusted under 35 U.S.C. 154(b) by 0 days.

(21) Appl. No.: 13/340,088

(22) Filed: Dec. 29, 2011

(65) Prior Publication Data
US 2012/0172555 A1 Jul. 5, 2012

Related U.S. Application Data

(60) Provisional application No. 61/428,999, filed on Dec. 31, 2010.

(51) Int. Cl.
*C07C 309/00* (2006.01)

(52) U.S. Cl.
USPC ........................................................ 562/108

(58) Field of Classification Search
None
See application file for complete search history.

(56) References Cited

U.S. PATENT DOCUMENTS

| | | | |
|---|---|---|---|
| 2,964,557 | A | 12/1960 | Niederhauser et al. |
| 3,759,985 | A | 9/1973 | Nukina et al. |
| 5,945,250 | A | 8/1999 | Aoai et al. |
| 7,776,510 | B2 | 8/2010 | Iwai et al. |
| 7,833,690 | B2 | 11/2010 | Gonsalves et al. |
| 2009/0202943 | A1 | 8/2009 | Ohsawa et al. |
| 2009/0269696 | A1 | 10/2009 | Ohsawa et al. |
| 2010/0040977 | A1 | 2/2010 | Nagai et al. |
| 2010/0063232 | A1 | 3/2010 | Nagai et al. |
| 2011/0015431 | A1 | 1/2011 | Jodry et al. |
| 2011/0177453 | A1 | 7/2011 | Masubuchi et al. |
| 2012/0171616 | A1* | 7/2012 | Thackeray et al. ........ 430/285.1 |

FOREIGN PATENT DOCUMENTS

| | | | | |
|---|---|---|---|---|
| EP | 2020616 | A2 | 2/2009 | |
| EP | 2080774 | A1 | 7/2009 | |
| EP | 2088467 | * | 8/2009 | .............. G03F 7/004 |
| EP | 2088467 | A1 | 8/2009 | |
| EP | 2090931 | A1 | 8/2010 | |
| EP | 2341089 | A1 | 7/2011 | |
| JP | 2006219419 | A | 8/2009 | |
| JP | 2010024215 | A | 2/2010 | |
| WO | 2009152276 | A2 | 12/2009 | |
| WO | 2010026973 | A1 | 3/2010 | |

OTHER PUBLICATIONS

U.S. Appl. No. 13/339,831, filed Dec. 29, 2011.
U.S. Appl. No. 13/339,948, filed Dec. 29, 2011.
CN 101687740 A; Date of Publication Mar. 31, 2010; English Abstract; 2 pages.
CN 101799629 A; Date of Publication Aug. 11, 2010; English Abstract; 2 pages.
European Search Report; European Application No. 11195705.6; Date of Mailing; May 12, 2012; Date Received: May 21, 2012, 3 pages.
JP 2006219419 A; Date of Publication Aug. 24, 2006; English Abstract; 1 page.
WO 2009019793 A1; Date of Publication Feb. 12, 2009; English Abstract; 2 pages.
WO 2009037980 A1; Date of Publication Mar. 26, 2009; English Abstract; 2 pages.
JP 2010024215 A; Date of Publication Feb. 4, 2010; English Abstract; 2 pages.
European Search Report dated Dec. 14, 2012; Application No. 11195707.2; 4 pages.
JP 2006178317 A; Jul. 6, 2006; Machine Translation; 100 pages.
Lee, C.T. et al. "The effect of direct PAG incoproation into the polymer main chain on reactive ion etch resistance of 193 nm and EUV chemically amplified resists." Microelectronic Engineering:2008. pp. 963-965. vol. 85.
Li-Qing Hu et al. "Synthesis of Perhaloalkanesulfonyl Halides and Their Sulfonimide Derivatives." Inorg. Chem. 1993. pp. 5007-5010. vol. 32.
Prakash, G.K. et al. "Preparation of x, x-difluoroalkanesulfonic acids." Journal of Fluorine Chemistry: 2004. pp. 595-601. vol. 125.
Huang et al., Inorg. Chem., 1991, 30, 789-794.
Benrabah et al., "Perfluorosulfonate-Polyether Based Single Ion Conductors", Electrochimica Acta, 40(13-14), 1995, pp. 2259-2264.
Ritter et al., "Synthesis and characterization of thiophenes with fluorinated substituents", Journal of Fluorine Chemistry, 93, 1999, pp. 73-79.

* cited by examiner

*Primary Examiner* — Noble Jarrell
(74) *Attorney, Agent, or Firm* — Cantor Colburn LLP

(57) ABSTRACT

A monomer compound has the formula (I):

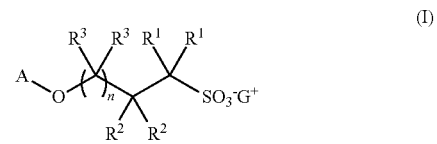

where each $R^1$, $R^2$, and $R^3$ is independently H, F, $C_{1-10}$ alkyl, fluoro-substituted $C_{1-10}$ alkyl, $C_{1-10}$ cycloalkyl, or fluoro-substituted $C_{1-10}$ cycloalkyl, provided that at least one of $R^1$, $R^2$, or $R^3$ is F; n is an integer of from 1 to 10, A is a halogenated or non-halogenated $C_{2-30}$ olefin-containing polymerizable group, and $G^+$ is an organic or inorganic cation. The monomer is the reaction product of a sultone precursor and the oxyanion of a hydroxy-containing halogenated or non-halogenated $C_{2-30}$ olefin-containing compound. A polymer includes the monomer of formula (I).

6 Claims, 2 Drawing Sheets

PHOTOACID GENERATING MONOMER AND PRECURSOR THEREOF

CROSS-REFERENCE TO RELATED APPLICATION

This application is a nonprovisional filing of U.S. provisional application No. 61/428,999 filed on Dec. 31, 2010, the content of which is incorporated herein by reference in its entirety.

BACKGROUND

Disclosed is a polymerizable photoacid generating monomer, and a sultone precursor compound for the monomer.

Advanced photolithographic techniques for imprinting desired patterns on silicon wafers generally rely upon acid-catalyzed deprotection of esters to acids in the poly(meth-acrylate) photoresist polymers as the key chemical reaction for transferring the pattern in order to induce a solubility change. This catalytic process, referred to as chemical amplification, is induced by irradiation of a photo-sensitive reagent or photoacid generator (PAG). PAGs used in photoresist polymers may consist of two parts: a sulfonate anion, and a tris(hydrocarbyl)sulfonium cation which usually has at least one aromatic group, where the cation absorbs a photon and decomposes to generate one acid proton, which leads to multiple desirable acid-catalyzed chemical reactions. Sulfonic acid superacids, e.g., alkyl or arylsulfonic acids having fluorine substituents generally within 2 or 3 bond lengths of the sulfur atom, are preferred in some applications.

As advances in photolithographic techniques lead to patterns with increasingly finer resolution, acid diffusion in the photoresist matrix becomes a concern. Acid diffusion may be impeded by, in one approach, tethering the conjugate base of the acid (e.g., a sulfonate anion) to the polymer, restricting the acid to a limited volume and more evenly distributing the PAG in the photoresist matrix.

U.S. Patent Application Publication No. 2009/0202943 A1 discloses a positive-tone resist which includes a polymer prepared from an acrylate or methacrylate monomer having a photoactive sulfonium fluoroalkylsulfonate salt (i.e., the conjugate base of a superacid) tethered to it through a (meth)acrylate monomer linkage. One exemplary such monomer is prepared by condensing the triaryl sulfonium salt of 1,1-difluoro-2-hydroxyethylsulfonate with (meth)acrylic anhydride. While such a condensation can in principle be used, the synthesis of the anion involves a three-step synthesis from commercially available precursors, and the precursors are limited due to the possibility of side-reactions with the cation and/or the polyfunctional anion.

STATEMENT OF INVENTION

The above and other deficiencies of the prior art may be overcome by a compound having the formula (I):

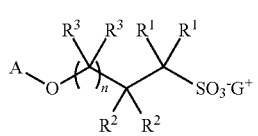

(I)

wherein each $R^1$, $R^2$, and $R^3$ is independently H, F, $C_{1-10}$ alkyl, fluoro-substituted $C_{1-10}$ alkyl, $C_{1-10}$ cycloalkyl, or fluoro-substituted $C_{1-10}$ cycloalkyl, provided that at least one of $R^1$, $R^2$, or $R^3$ is F; n is an integer of from 1 to 10, A is a halogenated or non-halogenated $C_{2-30}$ olefin-containing polymerizable group, and $G^+$ is an organic or inorganic cation.

A polymer comprises the compound of formula (I).

A sultone precursor for a monomer has the formula (XVI):

(XVI)

wherein each R is independently F, $C_{1-10}$ alkyl, fluoro-substituted $C_{1-10}$ alkyl, $C_{1-10}$ cycloalkyl, or fluoro-substituted $C_{1-10}$ cycloalkyl, provided that at least one R is F; n is an integer of from 0 to 10, and m is an integer of 1 to 4+2n.

A monomer comprises the reaction product of the sultone precursor and an oxyanion of a hydroxy-containing or carboxy-containing halogenated or non-halogenated $C_{2-30}$ olefin-containing compound.

BRIEF DESCRIPTION OF THE DRAWINGS

The foregoing and other objects, features, and advantages of the invention are apparent from the following detailed description taken in conjunction with the accompanying drawings in which.

DETAILED DESCRIPTION

Figure 1:
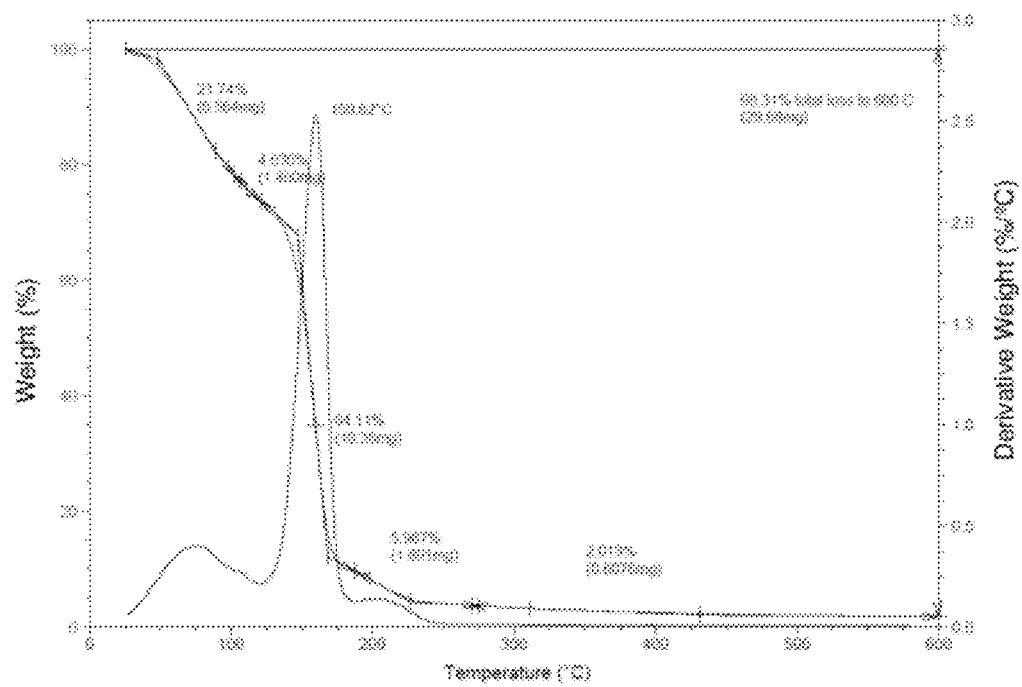
FIG. 1 shows a thermogravimetric analysis plot of mass loss versus temperature for an exemplary monomer.

Disclosed herein is a sultone precursor for a monomer, and novel olefinic monomers useful as photoacid generators (herein, PAGs) from fluorinated sultone precursors. As used herein, "sultone" refers to a cyclic sulfonate ester which is capable of undergoing ring-opening attack by addition of a nucleophile, where the ring-opening nucleophilic attack is specific to the carbon atom alpha to the sultone ring oxygen. Preferably, the sultone is fluorinated with one or more fluorine atoms, and still more preferably, the sultone may include a geminal difluoromethylene group alpha to the sulfonate sulfur atom. Where the nucleophile used in the ring-opening reaction is a carboxylic acid such as (meth)acrylic acid, or a hydroxystyrene or hydroxymethyl styrene, the product of the reaction with the sultone may be useful as a monomer for radical polymerization. The nucleophile, in these instances, may be the oxyanion of one of these compounds, and may be prepared by the reaction of a base with (meth)acrylic acid or styrene carboxylic acid, a hydroxystyrene (having a phenolic group) or a hydroxymethylstyrene (having a benzylic alcohol moiety).

The ring-opened product of the sultone is thus very cleanly obtained in high yield. A photoacid generator having low diffusion and low outgassing properties may further be prepared from the ring-opened product by metathesis in which the cation of the ring-opened product is exchanged for a photoactive cation, such as an onium cation having at least one phenyl group. Such a monomer, preferably when polymerized into a polymer and used in photoresist compositions generates acid when exposed to radiation for advanced lithographies such as for e-beam, x-ray, and extreme ultraviolet (EUV) radiation having a wavelength of 13.4-13.5 nm. Such monomers desirably have low acid diffusion, and can provide high contrast and good line shape. Further, the decomposition products of these PAGs may be reduced relative to conventional non-polymer bound PAGs, under similar conditions of photoresist composition, exposure, and processing.

As used herein "onium" refers to iodonium or sulfonium cations. Also as used herein, "substituted" means including a substituent such as a halogen (i.e., F, Cl, Br, I), hydroxy, amino, thiol, carboxyl, carboxylate, amide, nitrile, thiol, sulfide, disulfide, nitro, a $C_{1-10}$ alkyl, a $C_{1-10}$ alkoxy, a $C_{6-10}$ aryl, a $C_{6-10}$ aryloxy, a $C_{7-10}$ alkyl aryl, a $C_{7-10}$ alkyl aryloxy, or a combination comprising at least one of the foregoing. It will be understood that any group or structure disclosed with respect to the formulas herein may be so substituted unless otherwise specified, or where such substitution would significantly adversely affect the desired properties of the resulting structure. Also, "(meth)acrylate" as used herein means either acrylate or methacrylate, and is not limited to either of these unless otherwise specified.

The monomer is a compound having the general formula (I):

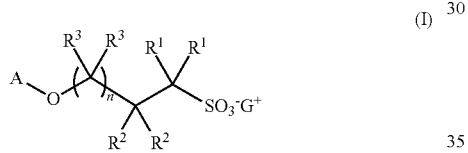

(I)

where each $R^1$, $R^2$, and $R^3$ is independently H, F, $C_{1-10}$ alkyl, fluoro-substituted $C_{1-10}$ alkyl, $C_{1-10}$ cycloalkyl, or fluoro-substituted $C_{1-10}$ cycloalkyl, provided that at least one of $R^1$, $R^2$, or $R^3$ is F. Exemplary groups $R^1$, $R^2$, and $R^3$ may include, in addition to one or more fluorine atoms, alkyl groups such as methyl, ethyl, n-propyl, isopropyl, n-butyl, 2-butyl, isobutyl, n-pentyl, 2-pentyl, 3-pentyl, 2-methylbutyl, 3-methylbutyl, n-hexyl, n-heptyl, n-octyl, 3-octyl, n-decyl, or any of the foregoing alkyl groups having one or more fluorine substituents including trifluoromethyl groups, 2,2,2-trifluoroethyl, perfluoroethyl, perfluorobutyl, or the like; or cycloalkyl groups such as cyclobutyl, cyclopentyl, 1-methylcyclopentyl, cyclohexyl, 1-methylcyclohexyl, 1- or 2-adamantyl, 1- or 2-decalinyl; or any of the foregoing cycloalkyl groups having one or more fluorine substituents including perfluorocyclopentyl, 3,5-bis(trifluoromethyl)cyclohexyl, perfluorocyclohexyl, or the like. More preferably, $R^1$, $R^2$, and $R^3$ are independently a combination of H and F.

Also in formula (I), n is an integer of from 1 to 10, and preferably, n is 1, 2, or 3. In formula (I), the total number of substituents $R^1$, $R^2$, and $R^3$ (other than hydrogen) may therefore be 4+2n. The monomer may include only a single $R^1$, $R^2$, or $R^3$ non-hydrogen substituent (where the substituent is F), or more than one substituent (other than hydrogen) is included in addition to the F group. Alternatively, substituents $R^1$, $R^2$, and $R^3$ are not F.

Also in formula (I), A is a halogenated or non-halogenated $C_{2-30}$ olefin-containing polymerizable group, and $G^+$ is an organic or inorganic cation.

In particular, A is the reaction residue of a nucleophile. While the nucleophile may include any nucleophilic group which can react with the precursor sultones disclosed hereinbelow, the nucleophile is preferably a polymerizable group which may react under polymerization conditions such as radical, anionic, cationic, or controlled free-radical polymerization methods to provide a polymer. Preferably, the nucleophile is the oxyanion of a hydroxy-containing halogenated or non-halogenated $C_{2-30}$ olefin-containing compound, where A is thus the reaction residue of the nucleophile which provides the halogenated or non-halogenated $C_{2-30}$ olefin-containing polymerizable group A.

Preferably, the nucleophile is the oxyanion of a $C_{3-20}$ vinyl carboxylic acid, a hydroxy-containing $C_{5-20}$ vinyl carboxylate, or a $C_{7-20}$ vinyl hydroxyaromatic compound. Hydroxyaromatic compounds, where used, may include phenolic hydroxy groups, or non-phenolic hydroxy groups such as benzylic hydroxy groups, or pendant hydroxy groups.

Exemplary nucleophiles include the oxyanion of unsaturated carboxylic acids such as (meth)acrylic acid, (meth)acryloyl acetic acid, maleic or fumaric acid, citraconic acid, itaconic acid, hydroxyl-containing (meth)acrylate esters such as 2-hydroxyethyl (meth)acrylate and 2-hydroxypropyl (meth)acrylate, carboxylic acids of norbornenes such as 5-norbornene-2-carboxylic acid and 5-norbornene-2,3-dicarboxylic acid, hydroxyl-containing (meth)acrylate esters such as 2-hydroxyethyl (meth)acrylate and 2-hydroxypropyl (meth)acrylate; hydroxystyrenes such as o, m, or p-hydroxystyrene, or vinylbenzyl alcohols such as 4-vinyl benzyl alcohol.

Preferably, the compound has the formula (II) or (III):

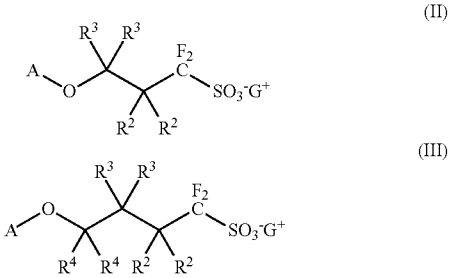

wherein each $R^2$, $R^3$, and $R^4$ is independently H, F, $C_{1-10}$ alkyl, or $C_{1-10}$ fluoroalkyl, n is 1 or 2, A-O is a $C_{3-20}$ vinyl carboxylate group, a hydroxy-containing $C_{5-20}$ vinyl carboxylate group, or a $C_{7-20}$ vinyl aryloxy compound, and $G^+$ is an organic or inorganic cation.

More preferably, the compound has the formula (IV), (V), (VI), (VII), or (VIII):

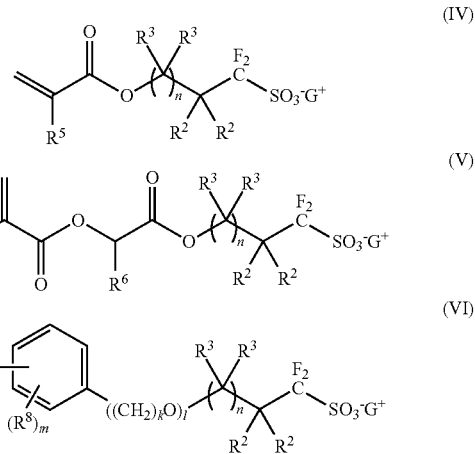

-continued

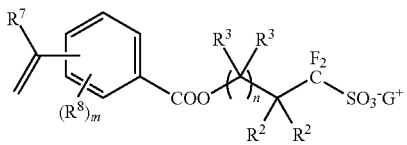
(VII)

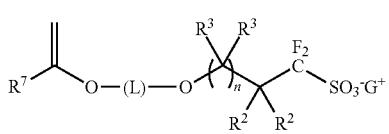
(VIII)

wherein each $R^2$, $R^3$, $R^4$, $R^5$, $R^6$, and $R^7$ is independently H, F, $C_{1-10}$ alkyl, or fluoro-substituted $C_{1-10}$ alkyl, each $R^8$ is independently F, $C_{1-10}$ alkyl, or fluoro-substituted $C_{1-10}$ alkyl, L is a halogenated or non-halogenated $C_{1-30}$ alkylene group, $C_{2-30}$ alkenylene group, monocyclic or polycyclic $C_{3-30}$ cycloalkylene group, monocyclic or polycyclic $C_{6-30}$ arylene group, or monocyclic or polycyclic $C_{7-30}$ alkylene-arylene group; k and l are each independently integers of 0 to 5 and where k is 0, l is 1; m is an integer of 0 to 4; n is 1, 2, or 3; and $G^+$ is an organic or inorganic cation.

The compound may more preferably be of the formula (IX), (X), (XI), (XII), or (XIII):

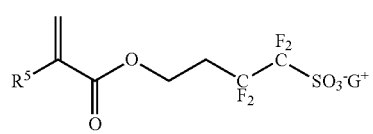
(IX)

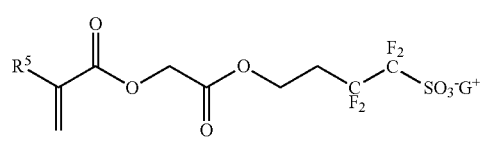
(X)

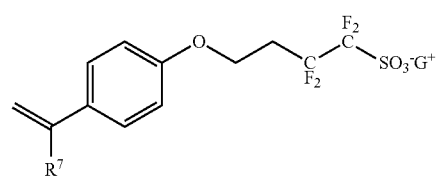
(XI)

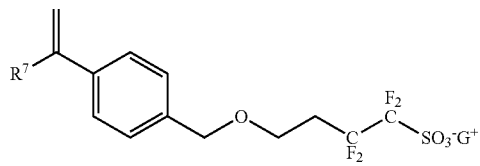
(XII)

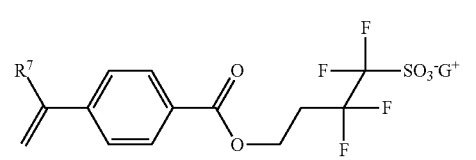
(XIII)

wherein $R^5$ and $R^7$ are independently H, F, $C_{1-10}$ alkyl, or fluoro-substituted $C_{1-10}$ alkyl, and $G^+$ is an organic or inorganic cation. Preferably, $R^5$ and $R^7$ are independently H or —$CH_3$.

The monomer, in addition to the anionic structure provided by the reaction of the sultone with the nucleophile, includes a cation $G^+$ where the cation may be any cation associated with the nucleophile (i.e., as the cation of the salt of the nucleophile). In this way, the cation may be, for example, an inorganic cation including an alkali metal cation, such as lithium, sodium, potassium, rubidium, cesium, an alkaline earth metal cation such as magnesium, calcium, barium, or strontium; a main group metal cation such as aluminum, tin, lead, or bismuth, or a transition metal cation such as copper, zinc, iron, nickel, cobalt, or silver; or the cation may be an organic cation such as an ammonium cation including ammonium, alkylammonium including mono-, di-, tri-, and tetraalkylammonium such as triethylammonium, tetramethylammonium, tetrabutylammonium, trimethylbenzylammonium, or cetylammonium; an iminium ion; a guanidinium ion, an alkylphosphonium cation; or an onium cation of iodine or sulfur substituted with alkyl, aryl, or aralkyl groups. A combination comprising at least one of the foregoing may be used. Preferably, the cation is an onium cation which is photodecomposable, and hence the monomer is also photodecomposable, i.e., is a photoacid generator (PAG) monomer.

The PAG monomers disclosed herein are based on a cation-anion structure in which the cation is preferably an aryl-substituted onium (i.e., disubstituted iodonium or trisubstituted sulfonium) cation, such as a triphenyl sulfonium cation, or of a structure in which the substituent aryl groups are further attached to one or more adjacent aryl groups in, for example, a heterocycle structure which includes the onium, or as part of a fused aromatic ring system.

Where the monomer is photodecomposable, i.e., where the reaction product of the oxyanion nucleophile and the sultone is a salt having a first, non-photodecomposable cation, the method further comprises exchanging the first, non-photodecomposable cation for a second cation of the formula (XIV):

(XIV)

wherein X is S or I, each $R^0$ is independently a halogenated or non-halogenated group comprising a $C_{1-30}$ alkyl group; a polycyclic or monocyclic $C_{3-30}$ cycloalkyl group; a polycyclic or monocyclic $C_{6-30}$ aryl group; or a combination comprising at least one of the foregoing, and optionally two $R^0$ groups are further attached to one another by a single bond where each $R^0$ is independently a monocyclic $C_{6-30}$ aryl group, and a is 2 or 3, where when X is I, a is 2, or when X is S, a is 3.

Preferably, G has the formula (XV), (XVI), or (XVII):

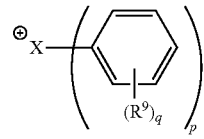
(XV)

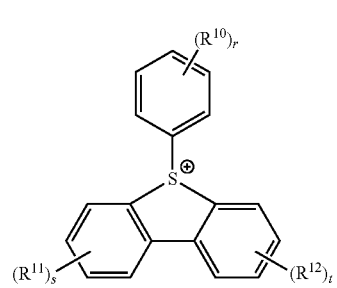
(XVI)

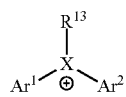
(XVII)

wherein X is I or S, $R^9$, $R^{10}$, $R^{11}$, and $R^{12}$ are each independently hydroxy, nitrile, halogen, $C_{1-10}$ alkyl, $C_{1-10}$ fluoroalkyl, $C_{1-10}$ alkoxy, $C_{1-10}$ fluoroalkoxy, $C_{6-20}$ aryl, $C_{6-20}$ fluoroaryl, $C_{6-20}$ aryloxy, or $C_{6-20}$ fluoroaryloxy, $Ar^1$ and $Ar^2$ are independently $C_{10-30}$ fused or singly bonded polycyclic aryl groups; $R^{13}$ is a lone pair of electrons where X is I, or a $C_{6-20}$ aryl group where X is S; and p is an integer of 2 or 3, wherein when X is I, p is 2, and where X is S, p is 3, q and r are each independently an integer from 0 to 5, and s and t are each independently an integer from 0 to 4.

Exemplary PAG cations $G^+$ include the following structures:

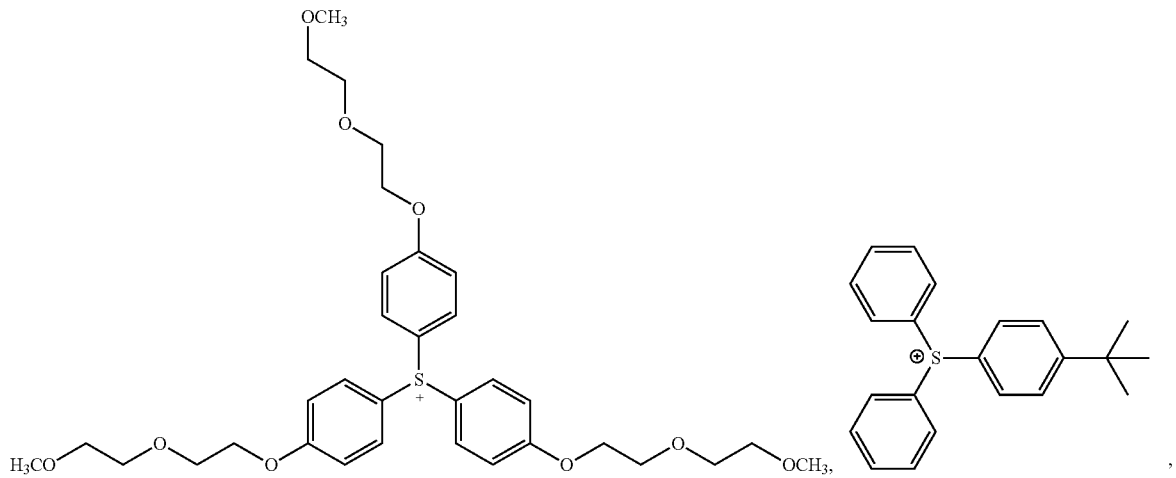

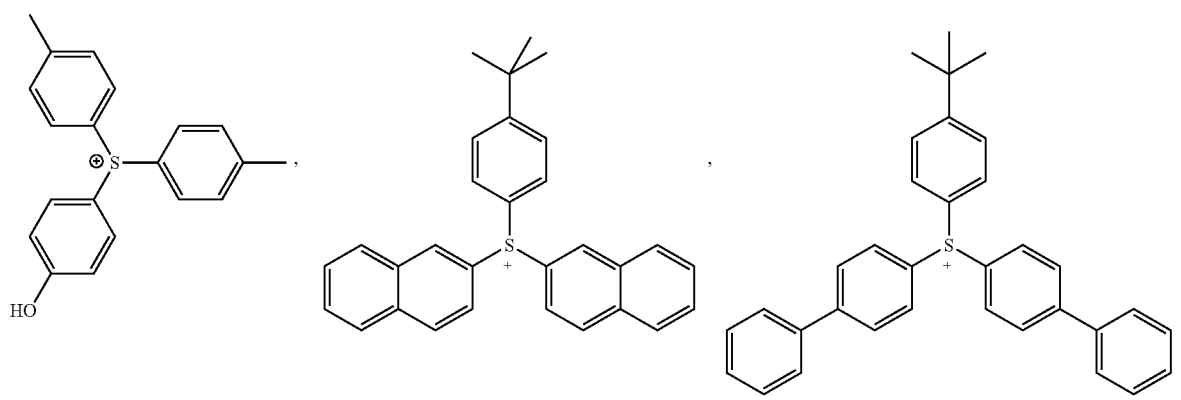

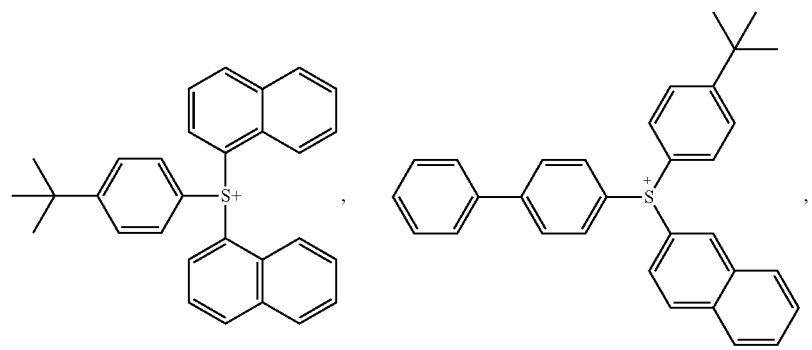

-continued
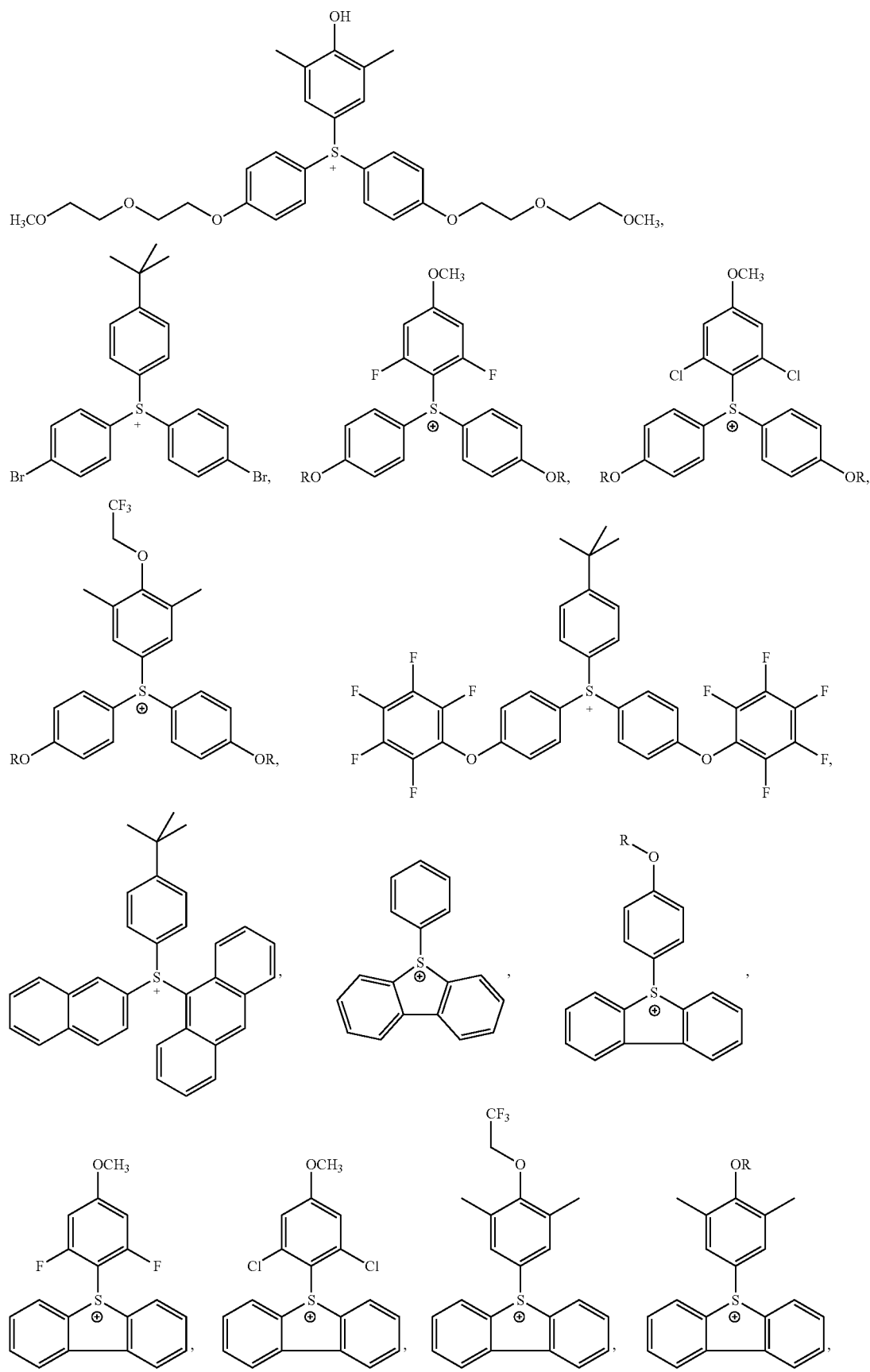

-continued
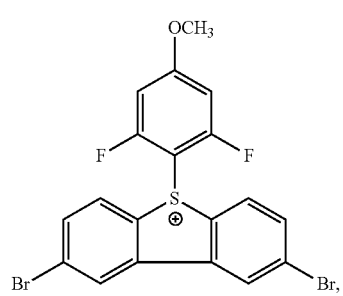
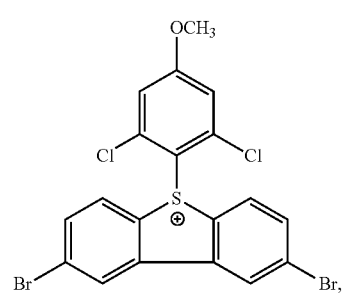
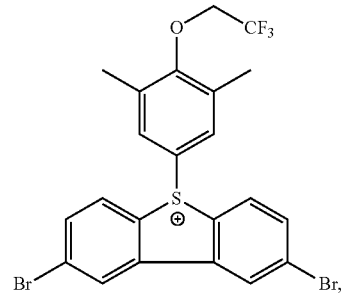
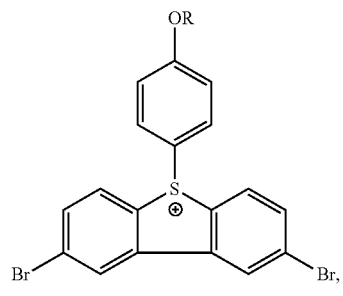
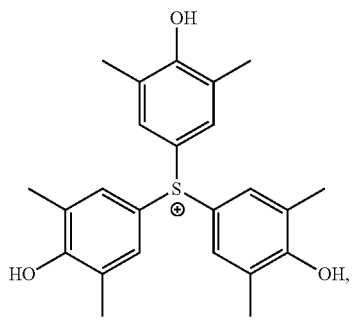
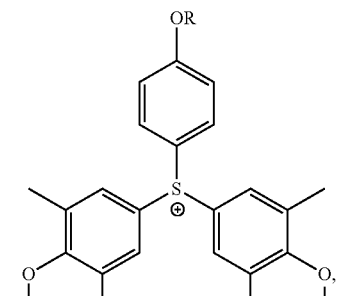
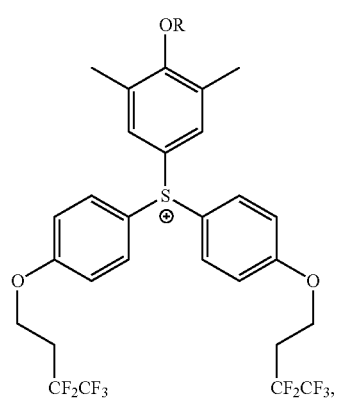
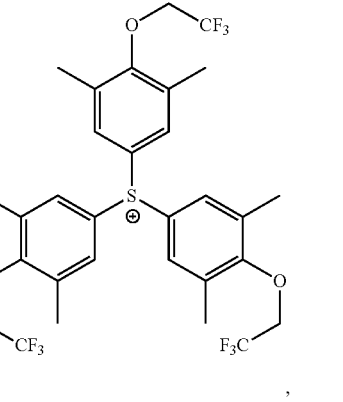
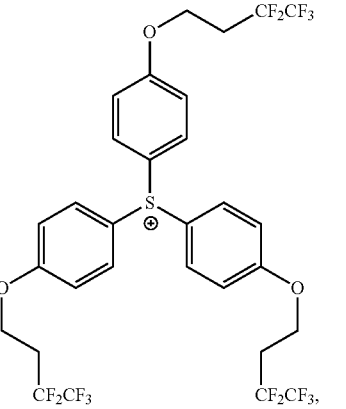
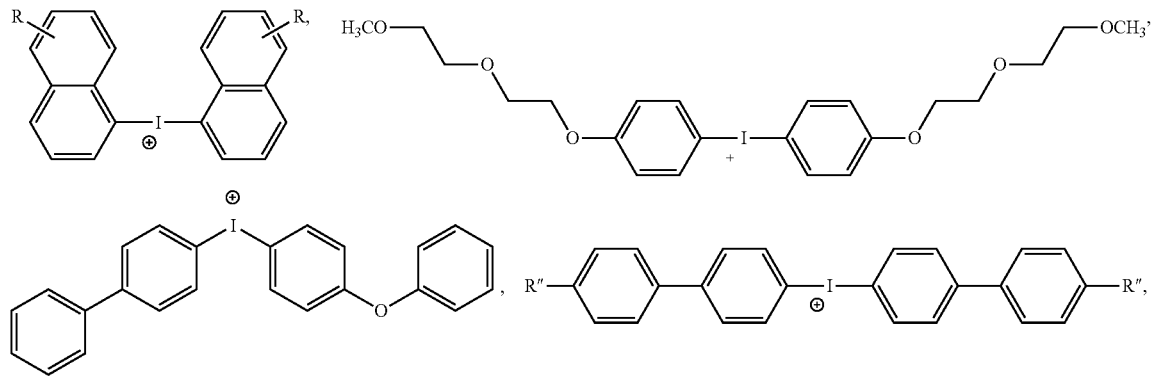
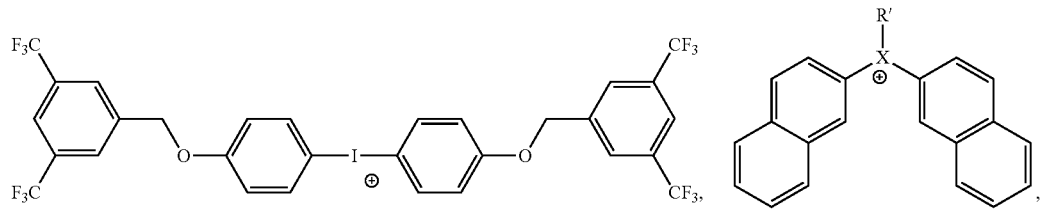

-continued
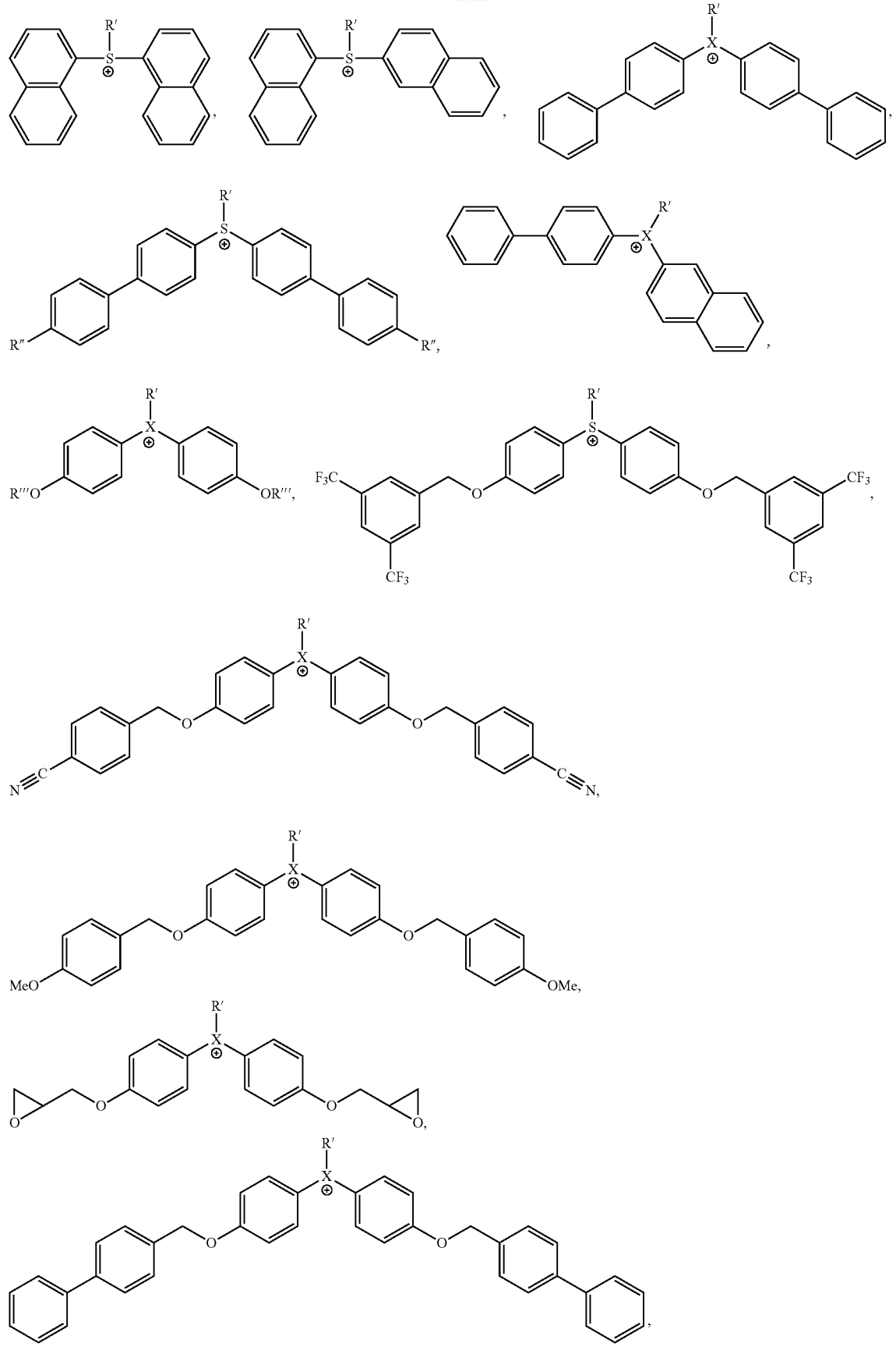

-continued
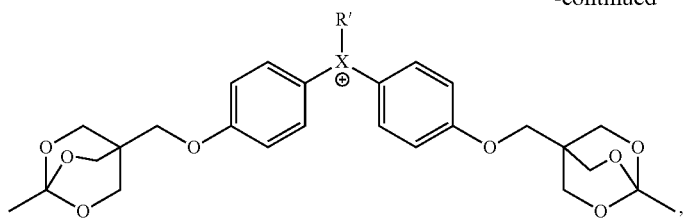
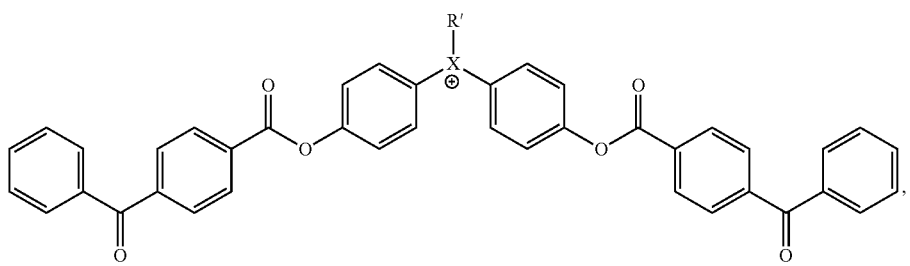
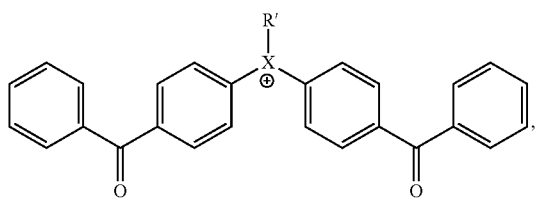
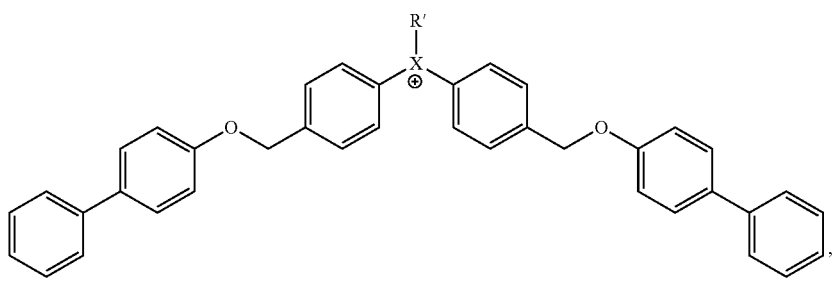
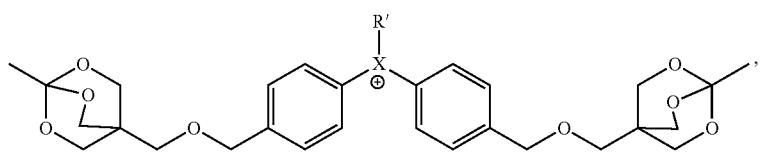
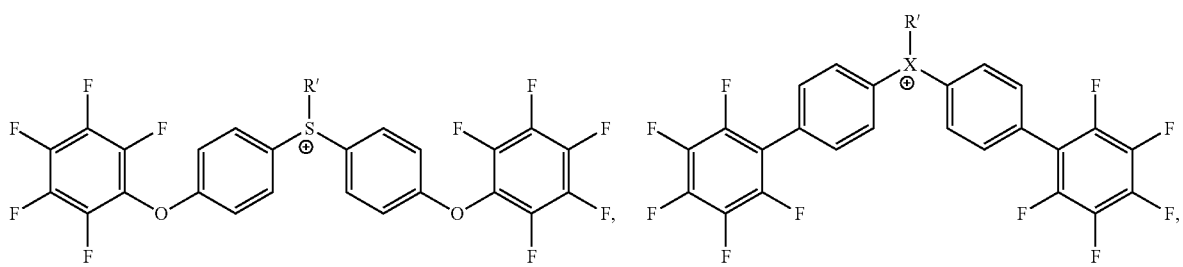
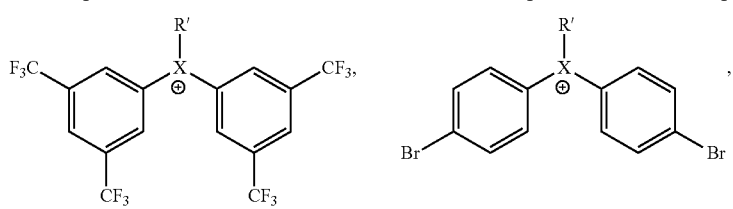

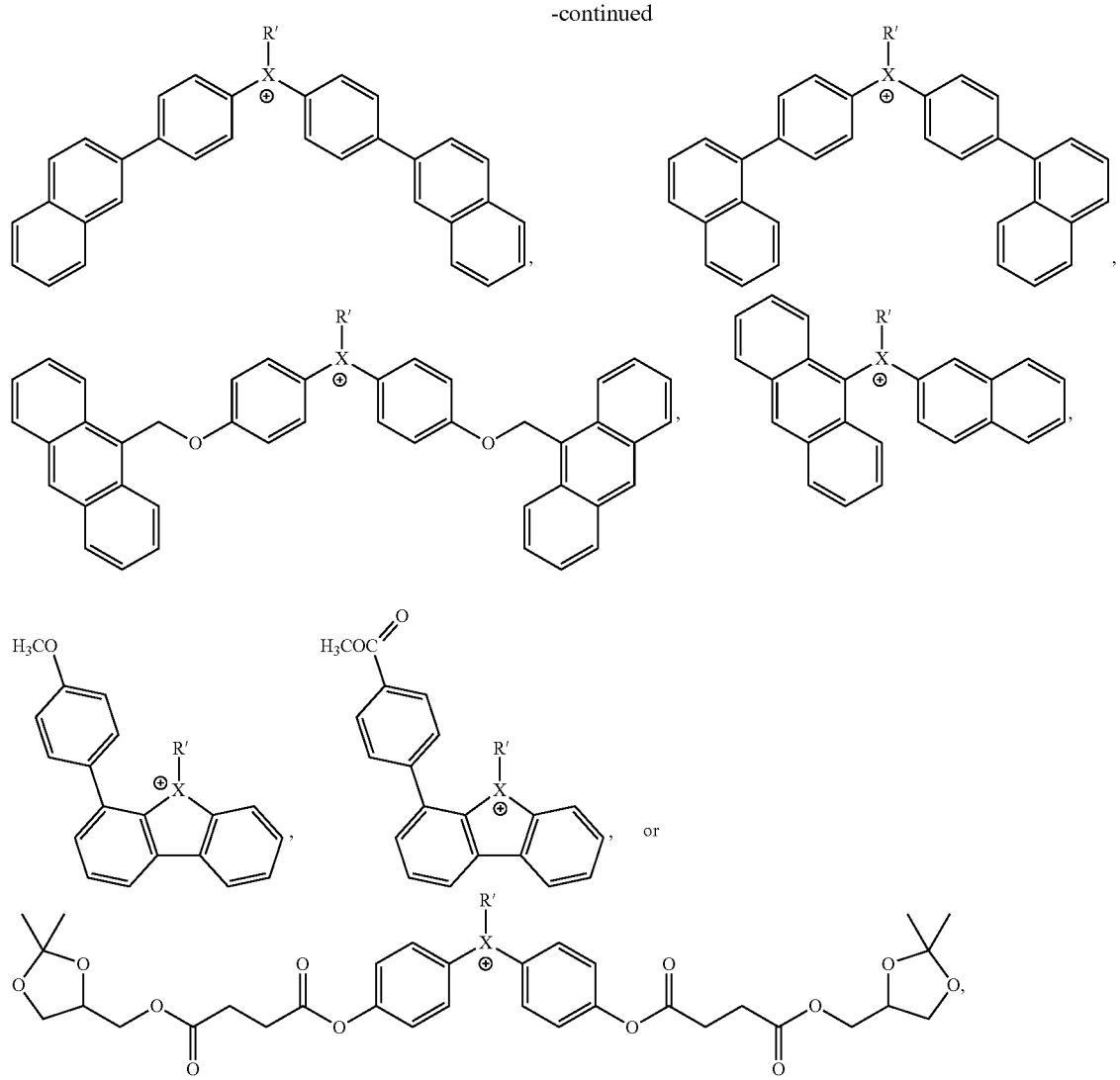

wherein X is S or I provided that where X is I, R' is a lone pair of electrons, R is $C_{1-10}$ alkyl, $C_{1-10}$ fluoroalkyl, $C_{1-10}$ alkoxy, or $C_{1-10}$ fluoroalkoxy group, where X is S, R' is a $C_{6-30}$ aryl, $C_{6-30}$ arylene, or $C_{7-20}$ alkyl-aryl group, each R" is independently H, OH, halogen, $C_{1-20}$ alkyl, $C_{1-20}$ fluoroalkyl, $C_{1-20}$ alkoxy, $C_{1-20}$ fluoroalkoxy, $C_{3-20}$ cycloalkyl, $C_{3-20}$ fluorocycloalkyl, $C_{6-20}$ aryl, $C_{7-20}$ alkyl-aryl, or a combination comprising at least one of the foregoing, and each R'" is independently H, $C_{1-20}$ alkyl, $C_{1-20}$ fluoroalkyl, $C_{1-20}$ alkoxy, $C_{1-20}$ fluoroalkoxy, $C_{3-20}$ cycloalkyl, $C_{3-20}$ fluorocycloalkyl, $C_{6-20}$ aryl, $C_{7-20}$ alkyl-aryl, or a combination comprising at least one of the foregoing.

Exemplary monomers of general formula (I) include:

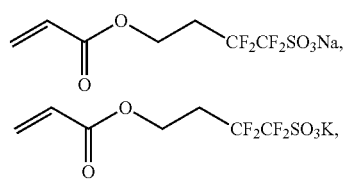

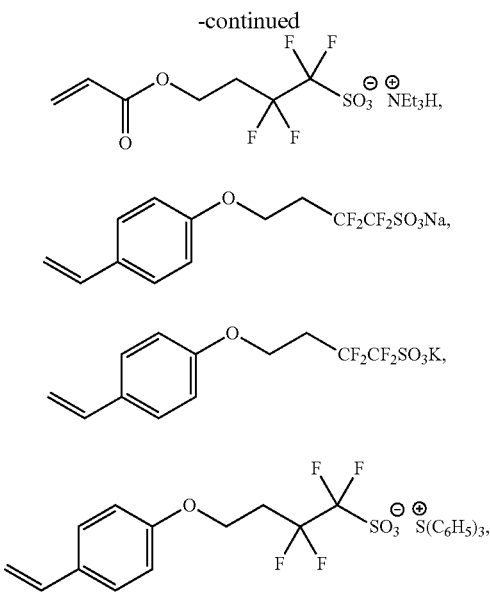

-continued

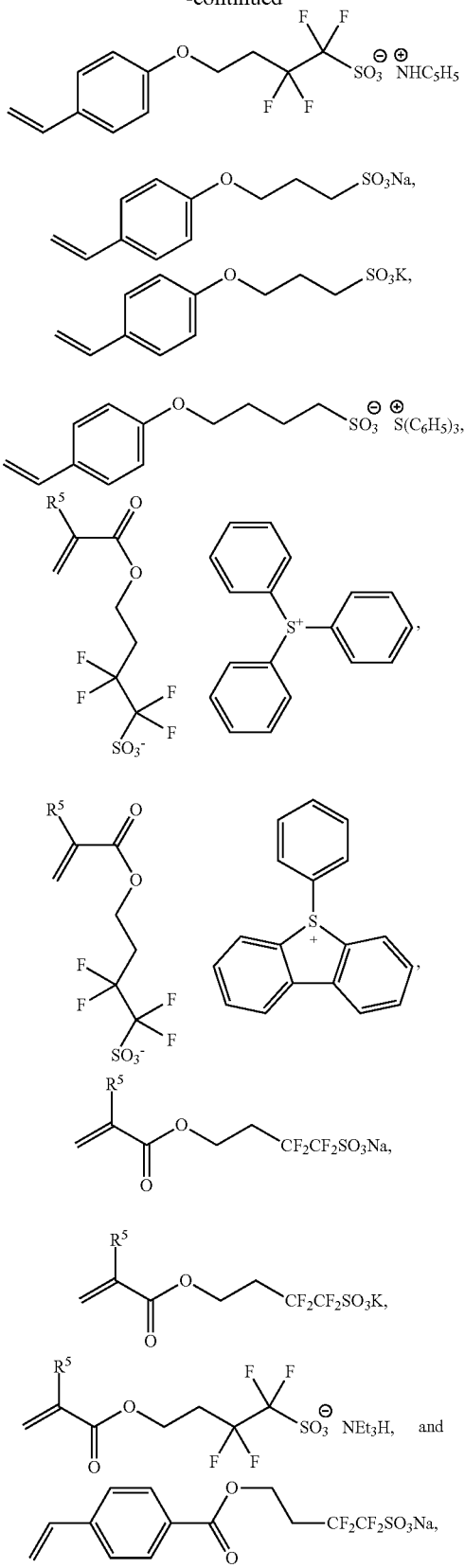

wherein $R^5$ is H, F, $C_{1-6}$ alkyl, or $C_{1-6}$ fluoroalkyl. Preferably, $R^5$ is H or —$CH_3$.

The foregoing monomers may be prepared from a precursor sultone of the formula (XVIII):

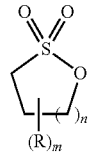

(XVIII)

with a nucleophile having a polymerizable group. In formula (XVIII), each R is independently F, $C_{1-10}$ alkyl, fluoro-substituted $C_{1-10}$ alkyl, $C_{1-10}$ cycloalkyl, or fluoro-substituted $C_{1-10}$ cycloalkyl, provided that at least one R is F. It will be generally understood herein that where no R or other substituent is specified for a carbon atom, the valency of each such carbon atom is filled with a hydrogen atom(s). Exemplary groups R may include, in addition to one or more fluorine atoms, alkyl groups such as methyl, ethyl, n-propyl, isopropyl, n-butyl, 2-butyl, isobutyl, n-pentyl, 2-pentyl, 3-pentyl, 2-methylbutyl, 3-methylbutyl, n-hexyl, n-heptyl, n-octyl, 3-octyl, n-decyl, or any of the foregoing alkyl groups having one or more fluorine substituents including trifluoromethyl groups, 2,2,2-trifluoroethyl, perfluoroethyl, perfluorobutyl, or the like; or cycloalkyl groups such as cyclobutyl, cyclopentyl, 1-methylcyclopentyl, cyclohexyl, 1-methylcyclohexyl, 1- or 2-adamantyl, 1- or 2-decalinyl; or any of the foregoing alkyl groups having one or more fluorine substituents including perfluorocyclopentyl, 3,5-bis(trifluoromethyl)cyclohexyl, perfluorocyclohexyl, or the like. More preferably, R is F.

Also in formula (XVIII), n is an integer of from 0 to 10, and preferably, n is 1, 2, or 3. The sultone may include m substituents R, where m is an integer of 1 to 4+2n. The sultone may include only a single R group substituent (where the substituent is F, and n is 1), or more than one substituent may be included in addition to the F group, where the total number of substituents R is limited to the number of sultone ring carbon atoms 2+n in which each ring carbon has up to 2 substituents for a maximum of 2×(2+n) or 4+2n substituents. Preferably, the total number of substituents is defined where m is an integer of 1 to 4. Alternatively, m may be 0, and/or R is not F.

Preferably, the sultone is of the formulas (XIX), (XX), or (XXI):

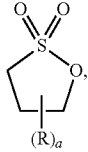

(XIX)

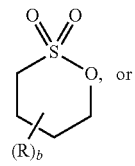

(XX)

, or (XXI)

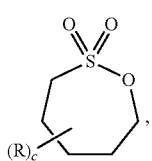

where each R is independently F, $C_{1-10}$ alkyl, or fluoro-substituted $C_{1-10}$ alkyl, provided that at least one R is F; a is an integer of 1 to 6, b is an integer of 1 to 8, and c is an integer of 1 to 10.

The sultone may more preferably be of the formula (XXII):

(XXII)

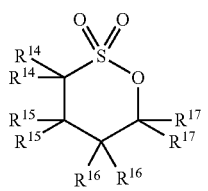

where $R^{14}$, $R^{15}$, $R^{16}$, and $R^{17}$ are each independently H, F, $C_{1-10}$ alkyl, or fluoro-substituted $C_{1-10}$ alkyl, provided that at least one of $R^{14}$, $R^{15}$, $R^{16}$, or $R^{17}$ is F. Preferably, at least one of $R^{14}$, $R^{15}$, or $R^{16}$ may be a fluorine atom, where each remaining $R^{14}$, $R^{15}$, and/or $R^{16}$ is H, and $R^{17}$ is H. Also preferably, both $R^{14}$, $R^{15}$, and/or $R^{16}$ are fluorine atoms, where any remaining $R^{14}$, $R^{15}$, and/or $R^{16}$ is H, and $R^{17}$ is H.

Still more preferably, the sultone may be of the formulas (XXIII) or (XXIV):

(XXIII)

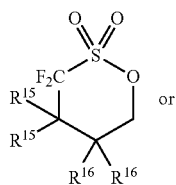

or (XXIV)

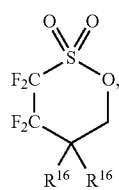

where $R^{15}$ and $R^{16}$ are each independently H, F, $C_{1-10}$ alkyl, or fluoro-substituted $C_{1-10}$ alkyl, provided that at least one of $R^{15}$ or $R^{16}$ is F. Preferably, at least one of $R^{15}$ or $R^{16}$ may be a fluorine atom, where each remaining $R^{15}$ and/or $R^{16}$ is H. Also preferably, both $R^{15}$ and/or $R^{16}$ include fluorine, where any remaining $R^{15}$ and/or $R^{16}$ is H.

Exemplary sultones of general formula (XVIII) include those of the formulas:

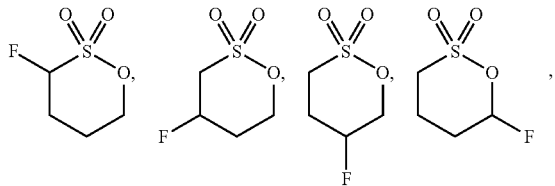

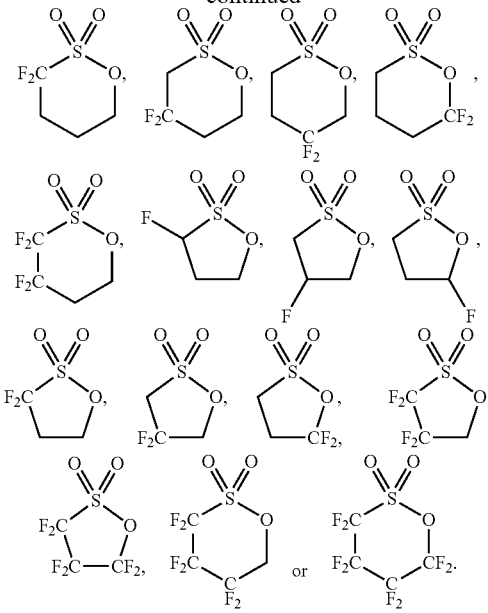

The sultones may themselves be generally prepared by dehydratively cyclizing a precursor alpha-omega alcohol-sulfonic acid compound in the presence of heat. The cyclization may be carried out at a temperature of up to 250° C., preferably 50 to 200° C. Heating at these temperatures may be for any time necessary to achieve cyclization in a sufficient yield. Azeotropic dehydration may also be used to remove water by distilling from a solution that forms a water azeotrope (such as using benzene/water or toluene/water), or reactive distillation with removal of water generated during cyclization may be used. Alternatively, a dehydrating agent such as 1,3-dicyclohexylcarbodiimide may be used, or the cyclization may be carried out under dehydrating acidic conditions such as with an anhydride (e.g., acetic anhydride) or sulfuric acid.

The alpha-omega sulfonic acid compounds which can be cyclized to form the sultones may themselves be prepared by methods such as by forming the sulfinic acid from the corresponding alpha-omega hydroxy-bromo compound. In this reaction, the bromine group is displaced by sodium dithionite ($Na_2S_2O_4$) in the presence of a weak base such as sodium bicarbonate to form the intermediate alpha-omega hydroxy sulfinate, followed by oxidation of the sulfinate to the corresponding sulfonate. Oxidation of the sulfinate may be carried out using any suitable method, such as oxidation with aqueous potassium permanganate or an aqueous solution of a peroxide such as hydrogen peroxide. The alpha-omega hydroxy sulfonate salt may then be converted to the corresponding sulfonic acid by treating directly with acid, or by protonation using a solid acid source such as a cation-exchange resin. Useful such resins include sulfonic acid strong cation exchange resins such as Amberlite™ 120H or Amberlyst™ 15H resins, available from Rohm and Haas Company.

The method of preparing the monomer includes reacting the sultone with a nucleophile as described hereinabove. Reacting, used in this context, means addition of the nucleophile to the carbon alpha to the sulfone oxygen, with ring opening of the sulfone. Preferably, the nucleophile is the oxyanion of a carboxy- or hydroxy-containing halogenated or non-halogenated $C_{2-30}$ olefin-containing compound. More preferably, the nucleophile is the oxyanion of a $C_{3-20}$ vinyl carboxylic acid, a $C_{8-20}$ vinyl aromatic carboxylic acid, a hydroxy-containing $C_{5-20}$ vinyl carboxylate, hydroxy-containing $C_{5-20}$ vinyl ether or precursor thereof, or a $C_{7-20}$ vinyl hydroxyaromatic compound. Hydroxyaromatic compounds, where used, may include phenolic hydroxy groups, or non-phenolic hydroxy groups such as benzylic hydroxy groups, or pendant hydroxy groups.

The oxyanion is formed by reacting a hydroxy-containing halogenated or non-halogenated $C_{2-30}$ olefin-containing compound with a base having a pKa for a conjugate acid thereof of greater than 12, provided the base used is sufficiently basic to effect deprotonation of the protonated precursor of the nucleophile, and provided the base is itself sufficiently non-nucleophilic so that significant reaction with other functionality in the nucleophile does not occur. Bases useful for this purpose may, depending on the acidity of the proton for the conjugate acid of the nucleophile, include carbonate bases such as lithium carbonate, sodium carbonate, potassium carbonate, rubidium carbonate, cesium carbonate, sodium hydrogen carbonate, and guanidinium carbonate; hydroxide bases such as lithium hydroxide, sodium hydroxide, potassium hydroxide, rubidium hydroxide, and cesium hydroxide; alkoxide bases such as sodium methoxide, sodium ethoxide, sodium isopropoxide, sodium t-butoxide, potassium methoxide, potassium ethoxide, potassium isopropoxide, potassium amylate, or potassium t-butoxide; amido bases such as lithium diisopropylamide, sodium diisopropylamide, potassium diisopropylamide, lithium hexamethylsilazide, sodium hexamethylsilazide, potassium hexamethylsilazide; amine bases such as trimethylamine, triethylamine, diethylisopropylamine, diisopropylamine, t-butylamine, proton sponge, cyclohexylamine, aniline, pyridine, N,N-dimethylaminopyridine, 4-pyrrolidinopyridine, pyrazine, pyrrole, piperidines, N-methyl piperidines, 2,2,6,6-tetramethylpiperidine, tetramethylethylene diamine, diaminocyclohexane, N,N,N'N'-tetramethylcyclohexane, diazabicyclononane (DBN), diazabicycloundecane (DBU), and Troger's base; hydride bases such as lithium hydride, sodium hydride, potassium hydride, rubidium hydride, cesium hydride, calcium hydride; Grignard reagents or organolithium reagents such as methyl magnesium chloride or n-butyllithium; alkali metals such as Li, Na, K, Rb, and Cs, either directly reacted with the precursor of the nucleophile or dissolved in a medium such as ammonia ($Li/NH_3$) or graphite (e.g., $KC_8$). Preferably, the oxyanion is generated by use of a hydroxide (e.g., NaOH or KOH), alkoxide (e.g., sodium ethoxide or potassium t-butoxide), carbonate (e.g., $Na_2CO_3$, or $NaHCO_3$) or hydride (NaH or KH) base. Where the oxyanion is the anion of a phenol or alcohol, the reaction conditions are most preferably deprotonation of the alcohol/phenol using NaH or KH in an aprotic, non-enolizable solvent.

Reacting of the sultone with the nucleophile may be carried out in a solvent. Useful solvents for this purpose may include water, ammonia, ethers such as ethyl ether, diisopropyl ether, methylphenyl ether, diphenyl ether, tetrahydrofuran, dioxane, or dioxolane; alcohols such as methanol, ethanol, isopropanol, t-butanol, 2-methylpropanol, methyl cellosolve, or ethyl cellosolve; acetonitrile; amides such as N,N-dimethylformamide, N,N-dimethyl acetamide, N-methylpyrrolidone, 1,3-dimethyl-2-imidazolidinone, and hexamethyl phosphoramide; dimethylsulfoxide, and sulfolane. Reacting conditions are not particularly limited and may be carried out at a temperature of up to about 250° C., and for a time suitable to effect ring-opening addition.

PAG cations may be included in the monomer may be performed by a cation exchange reaction, sometimes referred to herein a metathesis reaction, in which a first cation/anion pair $A^+C^-$ reacts with a second cation/anion pair $B+D^-$ in solution to form the exchanged products $A^+D^-$ and $B^+C^-$. Metathesis (i.e., ion exchange) reactions may be carried out, for example, in a biphasic medium where a low-activity cation/high-activity anion such as for example, triphenylsulfonium bromide, may be exchanged with a high-activity cation/low-activity anion such as, for example, the sodium or potassium salt of (4-sulfo-3,3,4,4-tetrafluorobutyl-2-methyl-2-propenoate). The biphasic medium may be any suitable biphasic medium, and preferably one having an aqueous phase for dissolving and removing the resulting high-activity salt (e.g., NaBr or KBr in the illustrative example) and an organic medium such as ether, or preferably dichloromethane, for dissolving and removing the low activity salt (e.g., the triphenylsulfonium salt of 4-sulfo-3,3,4,4-tetrafluorobutyl-2-methyl-2-propenoate). Exchange may be carried out at ambient temperature, for a time suitable to effect exchange equilibrium, where solvents, amounts, and times may be determined by the skilled artisan.

The monomers including the PAG monomers disclosed herein may be polymerized with comonomers suitable for copolymerization with them. Preferably, where the monomer is a PAG monomer, the PAG monomer is polymerized to form a copolymer with one or more comonomers having acid-sensitive groups, and optionally, with other comonomers to provide other properties such as etch control, dissolution rate control, and adhesion. Such copolymers may be useful in photoresists, preferably for EUV lithography, and may desirably have specific absorbance and decomposition characteristics when exposed to EUV radiation, over radiation of other wavelengths. For example, the EUV radiation source, in addition to an emission spectrum in the EUV region (about 12-14 nm, where the typical emission used is 13.4-13.5 nm) may emit at longer wavelengths to which photoacid generators may be sensitive, such as at 248 nm and/or 193 nm (which are also emission bands for KrF and ArF excimer lasers used in DUV and 193 nm lithographies).

The invention is further illustrated by the following examples.

All compounds used herein are available commercially except where a procedure is provided below. Nuclear magnetic resonance (NMR) spectra were obtained using a Varian INOVA 300 (FT 300 MHz, $^1H$; 282 MHz, $^{19}F$) spectrometer. Chemical shifts for $^1H$ and $^{19}F$ spectra were referenced internally to tetramethylsilane or to internal solvent resonances and are reported relative to tetramethylsilane. 4-Bromo-3,3,4,4-tetrafluoro-1-butanol was obtained from Synquest Laboratories. All other reagents, unless otherwise specified, were obtained from Aldrich. Solvents were obtained from Aldrich or Fisher Scientific.

Thermogravimetric analysis (TGA) was obtained using a TA Instruments Q5000 Thermogravimetric Analyzer operating under nitrogen at a temperature ramp rate of 5° C./min.

X-ray crystallographic data was obtained using a Bruker SMART X2S benchtop crystallographic system. APEX2 Version 2009.9 software (Bruker AXS Inc.) was used for preliminary determination of the unit cell. Determination of integrated intensities and unit cell refinement were performed using SAINT Version 7.68A software (Bruker AXS Inc., 2009). Data were corrected for absorption effects with SAD-ABS Version 2008/1 software (Bruker AXS Inc.) using the multiscan technique.

Example 1

Preparation of 2-methyl-2-propenoic acid, 4-sulfo-3,3,4,4-tetrafluorobutyl ester, sodium salt (1:1)

A. Preparation of sodium 4-hydroxy-1,1,2,2-tetrafluorobutane-1-sulfinate intermediate

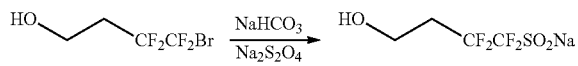

4-bromo-3,3,4,4-tetrafluoro-1-butanol (5.00 g, 22.2 mmol) was added to a slurry of $NaHCO_3$ (5.60 g, 66.67 mmol) and $Na_2S_2O_4$ (11.61 g, 66.67 mmol) in 15 mL of acetonitrile and 22 mL of water. The mixture was heated at about 55° C. for two days in a wax bath while stirring. The slurry was allowed to settle and an aliquot was removed which showed the reaction to be complete by $^1H$ NMR ($D_2O$). The reaction mixture was filtered and the volatiles were removed under reduced pressure on a rotary evaporator to provide the sulfinate salt intermediate as a white solid, which was placed back in the wax bath and heated over the weekend under reduced pressure at 80° C. A $^{19}F$ NMR spectrum confirmed the identity of the sulfinate salt intermediate. $^{19}F$ NMR ($D_2O$) d −112.55 (dd, 2F), −131.30 (dd, 2F).

B. Preparation of sodium 4-hydroxy-1,1,2,2-tetrafluorobutane-1-sulfonate intermediate (Small Scale)

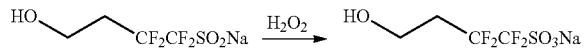

The above prepared solid was dissolved in 25 mL of water, cooled to 0° C. and 5 mL of 50% aqueous $H_2O_2$ (w/w) was added under generation of steam. After stirring for 1 hour, NMR spectra were taken of an aliquot which showed that the reaction was about 50% complete. Additional (5 mL) $H_2O_2$ was added and the stirring was continued. NMR analysis showed the reaction to be complete. The volatiles were removed under reduced pressure on a rotary evaporator to give a white solid. Peroxide test strips were used to confirm the presence of peroxide in the condensate, which was discarded, and in the solid which had been redissolved in water. Sodium bisulfite was added until no peroxide remained. The slurry was filtered and the volatiles were removed on a rotary evaporator to give the sulfonate salt as a white solid. $^{19}F$ NMR ($D_2O$) d −112.44 (dd, 2F), −117.08 (dd, 2F).

C. Preparation of sodium 4-hydroxy-1,1,2,2-tetrafluorobutane-1-sulfinate intermediate (Larger Scale)

4-Bromo-3,3,4,4-tetrafluoro-1-butanol (19.92 g, 88.54 mmol) was added to a slurry of $NaHCO_3$ (22.31 g, 265.6 mmol) and $Na_2S_2O_4$ (46.25 g, 265.6 mmol) in 60 mL of acetonitrile and 88 mL of water. The mixture was heated at about 55° C. for two days in a wax bath without stirring due to the large amount of solids present. $^{19}F$ NMR spectra showed almost no conversion to product. The temperature was then increased to about 80° C. As the temperature increased, sufficient of the inorganic salts ($NaHCO_3$ and $Na_2S_2O_4$) dissolved to allow for stirring of the mixture. Additional sodium dithionite (17 g) and sodium bicarbonate (15 g) were added. NMR spectra showed that further reaction had occurred. The reaction mixture was allowed to cool to ambient temperature and additional water (100 mL) and acetonitrile (100 mL) were added so that all the solid material dissolved. NMR spectra were taken of each layer. The aqueous layer contains sulfinate and perhaps a small amount of sulfonate, but no starting bromide, while no acetonitrile layer shows a considerable amount of starting material. The layers were separated. The aqueous layer was set aside, and additional sodium dithionite (30 g) and sodium carbonate (38 g) were added to the acetonitrile layer (200 mL) along with about 100 mL of water. The reaction mixture was heated at about 85° C. overnight. The solution was cooled, filtered, combined with the previously separated aqueous layer, and the volatiles were removed on a rotary evaporator. The resulting crunchy solid was washed with about 200 mL of ether and dried under vacuum.

D. Preparation of sodium 4-hydroxy-1,1,2,2-tetrafluorobutane-1-sulfonate intermediate (Larger Scale)

The above prepared solid was dissolved in 25 mL of water, cooled to 0° C. in an ice bath and 50 mL of aqueous 50% $H_2O_2$ (w/w) was added under generation of steam. The reaction mixture was allowed to stir overnight. $^{19}F$ NMR spectra showed the reaction to be about 90-95% complete. Additional (20 mL) of the $H_2O_2$ solution was added and the stirring was continued until NMR analysis showed the reaction to be complete. Sodium bisulfite was then added until no peroxide remained. The slurry was then filtered and the volatiles were removed on a rotary evaporator to give a white solid having the same characteristic properties as described in Example 1, part B.

E. Preparation of 4-hydroxy-1,1,2,2-tetrafluorobutane-1-sulfonic acid intermediate

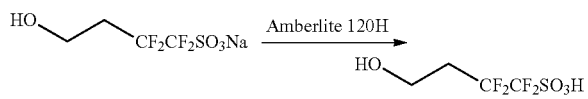

The white solid from Example 1, part D, which contained sodium 4-hydroxy-1,1,2,2-tetrafluorobutane-1-sulfonate, was extracted with methanol (ca. 200 mL) and filtered to remove particulates. The resulting pale yellow solution was passed through a column packed with about 8 cm of Amberlite™ 120H acidic cation exchange resin to provide a light brown solution of the protonated compound as the sulfonic acid. Additional methanol was used to flush out any remaining sulfonic acid. The volatiles were removed under reduced pressure to give a dark brown oil containing black particulate specks. The yield was 15.5 g, 77.2% based on starting 4-bromo-3,3,4,4-tetrafluoro-1-butanol.

The sulfonic acid was characterized by thermogravimetric analysis (TGA) under nitrogen atmosphere, and at a temperature ramp rate of 5° C./min. FIG. 1 shows the thermogravimetric (TGA) plot data, where it can be seen that decomposition of the sulfonic acid proceeds steadily with loss of about 30% mass until about 150° C. is reached, at which point decomposition accelerates with the maximum rate of decomposition occurring at a temperature of 159.6° C., and with the compound reaching complete loss of mass at a temperature of about 245° C.

F. Preparation of 3,3,4,4-tetrafluorobutanesultone

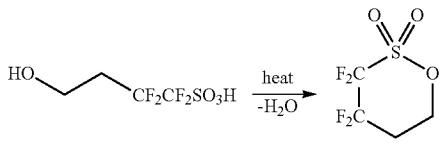

4-Hydroxy-1,1,2,2-tetrafluorobutane-1-sulfonic acid (2.00 g, 8.84 mmol) was placed in a 5-mL round-bottom flask attached to a short-path distillation column. The system was placed under a nitrogen atmosphere. The flask was immersed in a hot wax bath and the temperature was gradually raised from 130° C. to 180° C. While this temperature rise was occurring, water began to distill up into the cooler regions of the distillation apparatus. The apparatus was disassembled and the flask was reconnected to a microdistillation apparatus and heating under nitrogen was resumed. The pressure was gradually decreased so that the product sultone and water distilled over and formed a two-phase liquid product. The lower sultone layer was removed by pipette, dried over anhydrous magnesium sulfate, and filtered through a pipette filter to give the product as a colorless liquid.

G. Preparation of 3,3,4,4-tetrafluorobutanesultone (Larger Scale)

4-Hydroxy-1,1,2,2-tetrafluorobutane-1-sulfonic acid (6.78 g, 30.0 mmol) was placed in a 50-mL round-bottom flask attached via a V-tube to a Schlenk tube. The system was placed under vacuum and the Schlenk tube was immersed in liquid nitrogen. The flask containing the sulfonic acid was immersed in a hot wax bath and the temperature was gradually raised to about 160° C. The product sultone and water gradually distilled over and froze in the receiver vessel. After thawing, two layers formed. The lower sultone layer was removed by pipette, dried over anhydrous magnesium sulfate, and filtered to give the product as a colorless liquid (3.85 g, 61.7%).

H. Preparation of 2-methyl-2-propenoic acid, 4-sulfo-3,3,4,4-tetrafluorobutyl ester, sodium or potassium salt (1:1)

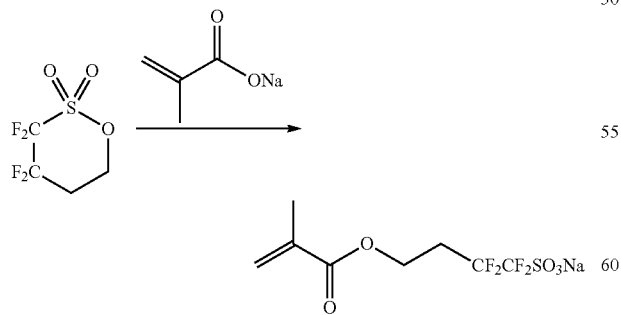

NMR tube scale, sodium salt (1:1): Sodium hydride (0.029 g, 1.2 mmol) was added slowly to methacrylic acid (0.103 g, 1.2 mmol) in 1 mL of CD$_3$CN. After stirring overnight, 3,3,4,4-tetrafluorobutanesultone (0.250 g, 1.2 mmol) was added and the mixture was transferred to an NMR tube. The reaction progress was monitored by $^1$H NMR. The mixture was gradually heated up to 75° C. at which time the reaction was complete.

Bulk scale, potassium salt (1:1): Methacrylic acid (1.708 g, 19.85 mmol) was added slowly to potassium hydride (1.150 g, 28.66 mmol) in 40 mL of THF. After stirring overnight, the reaction mixture was filtered and the volatiles were removed under reduced pressure. 3,3,4,4-Tetrafluorobutanesultone (3.260 g, 15.66 mmol), methacrylic acid (2.0 mL), and a small amount of hydroquinone were added to the potassium methacrylate and the mixture was then heated overnight at 75° C. Acetone (10 mL) was added to the mixture. The solids were filtered out and washed with additional acetone and dried under reduced pressure. The solids were then extracted with water and filtered. The volatiles were removed under reduced pressure to give a white crystalline solid (4.10 g, 78.8%).

Figure 2:
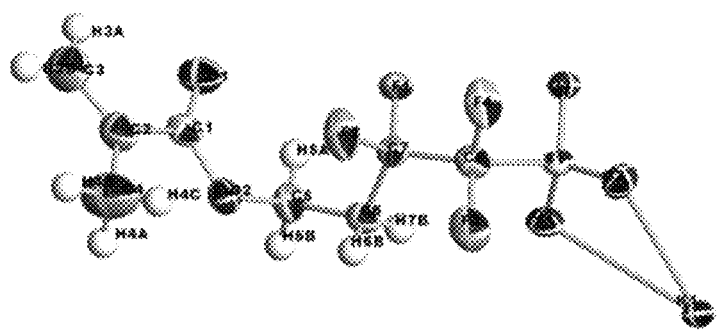
FIG. 2 is an ORTEP plot of the potassium salt of an exemplary monomer based on X-ray crystallographic analysis.

FIG. 2 shows an ORTEP plot of the structure of the product, 2-methyl-2-propenoic acid, 4-sulfo-3,3,4,4-tetrafluorobutyl ester, potassium salt (1:1). Crystals suitable for a single crystal x-ray diffraction study were grown by evaporation of an aqueous solution of the product of Example 1, part H (Bulk scale). The crystals grew in the form of flat colorless needles. The data sets were collected in a straightforward manner using a Bruker SMART X2S bench top crystallographic system. XPREP Version 2008/2 software (Bruker AXS Inc.) determined the space group to be P1 21/c 1, with Z=4 for the formula unit, $C_8H_9F_4KO_5S$. The structure was solved with XS Version 2008/1 software (Bruker AXS Inc.) and subsequent structure refinements were performed with XL Version 2008/4 software (Bruker AXS Inc.). The final anisotropic full-matrix least-squares refinement on $F_o^1$ with 173 variables converged at $R_1$=5.11% for the observed data and with $R_2$=16.75% for all data.

Example 2

Preparation of triphenylsulfonium 1,1,2,2-tetrafluoro-4-(methacryloyloxy)butane-1-sulfonate

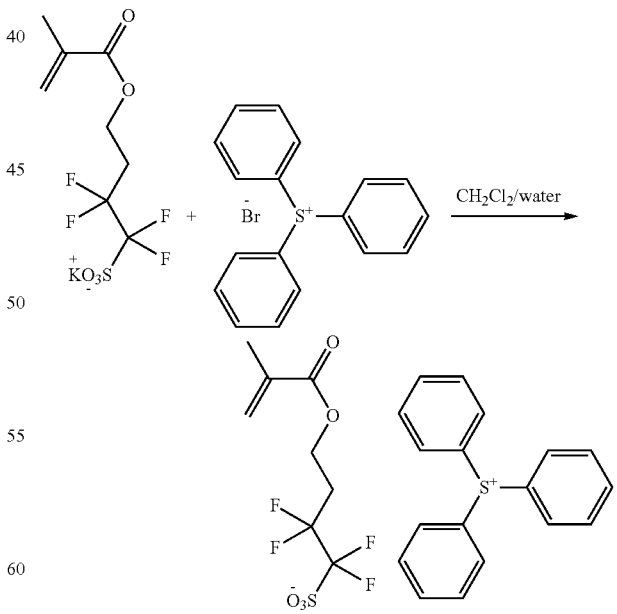

Potassium 1,1,2,2-tetrafluoro-4-(methacryloyloxy)butane-1-sulfonate (2 g, 6.02 mmol) and triphenylsulfonium bromide (2.25 g, 6.57 mmol) were added to a 100-mL round bottom flask, along with 15 mL of dichloromethane and 15 mL of distilled, deionized water. The mixture was vigorously stirred for 36 hours. Stirring was stopped and the mixture separated into two clear layers; the organic layer was washed twice with 30 mL of 1% (w/w) aqueous ammonium hydroxide and five times with 30 mL of distilled, de-ionized water. The organic layer was dried over sodium sulfate and filtered. Hydroquinone (1 mg) was added and the solvent was removed by rotary evaporation and high vacuum to yield the product as a colorless, viscous oil (2.65 g, 4.76 mmol). $^1$H NMR (d$_6$-acetone): 7.9 (br), 6.1 (s), 5.6 (s), 4.4 (t), 2.8 (m), 1.9 (s); $^{19}$F NMR (d$_6$-acetone): −112.7 (s), −119.7 (s).

Example 3

Preparation of phenyl dibenzothiophenium 1,1,2,2-tetrafluoro-4-(methacryloyloxy)butane-1-sulfonate

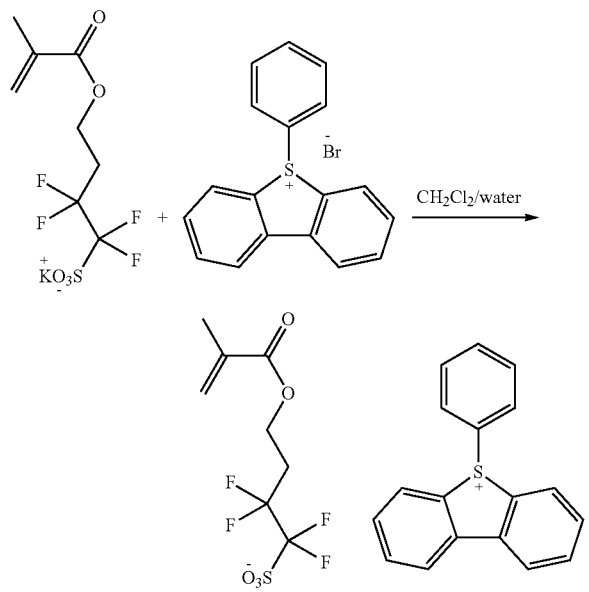

Potassium 1,1,2,2-tetrafluoro-4-(methacryloyloxy)butane-1-sulfonate (1.91 g, 5.75 mmol) and phenyl dibenzothiophenium bromide (2.14 g, 6.27 mmol) were added to a 100-mL round bottom flask, along with 15 mL of dichloromethane and 15 mL of distilled, de-ionized water. The mixture was vigorously stirred over the weekend. Stirring was stopped and the mixture separated into two clear layers; the organic layer was washed twice with 30 mL of 1% aqueous ammonium hydroxide and five times with 30 mL of distilled, deionized water. Dichloromethane was removed by rotary evaporation and high vacuum to yield the product as a white powder (2.41 g, 4.35 mmol). $^1$H NMR (d$_6$-acetone): 8.6 (d), 8.4 (d), 8.0 (t), 7.8 (br), 7.6 (t), 6.1 (s), 5.6 (s), 4.4 (t), 2.8 (m), 1.9 (s); $^{19}$F NMR (d$_6$-acetone): −112.7 (s), −119.8 (s).

Example 4

Copolymerization of triphenylsulfonium 1,1,2,2-tetrafluoro-4-(methacryloyloxy)butane-1-sulfonate
(Exemplary polymer)

2-Phenyl-2-propyl methacrylate (3.32 g, 16.25 mmol), alpha-(gammabutyrolactone) methacrylate (4.40 g, 23.75 mmol), 3,5-bis(1,1,1,3,3,3-hexafluoro-2-hydroxypropan-2-yl)cyclohexyl methacrylate (3.13 g, 6.25 mmol), and triphenylsulfonium 1,1,2,2-tetrafluoro-4-(methacryloyloxy)butane-1-sulfonate (50 wt. % solution in acetonitrile; 4.17 g, 3.75 mmol) were dissolved in 16.8 g of ethyl lactate/cyclohexanone (70/30 v/v). 2,2-Azobis(2,4-dimethylvaleronitrile) (1.24 g, 3.75 mmol) was dissolved in the monomer solution. A small amount (~5 mL) of monomer solution was introduced to a vessel pre-heated in an 80° C. oil bath and, after 5 min., the remainder of the monomer solution was fed into the vessel over 4 hours. The reaction mixture was heated for an additional 2 hours. The reaction solution was cooled to room temperature and precipitated into a 1 L mixture of agitated methyl t-butyl ether and 2-propanol (90/10 v/v). The resultant white powder polymer was isolated by vacuum filtration and dried in a vacuum oven at 45° C. for 48 hours (yield 7.3 g, 58%).

Evaluation of copolymer. DUV evaluation of a photoresist containing the polymer of Example 4. The polymer of Example 4 (0.61 g) was dissolved in 15.40 g of ethyl lactate and 3.82 g of cyclohexanone (70:30 w/w) and 0.12 g of a 1% (w/w) solution of tetramethylammonium salicylate in ethyl lactate and 0.06 g of a 1% (w/w) solution of POLYFOX 656 surfactant were added. The solution was filtered through a 0.2 micrometer TEFLON filter.

The above photoresist formulation was lithographically processed as follows. The formulated resist was spin-coated using TEL ACT-8 (Tokyo Electron) coating track onto a 200 mm silicon wafer having a bottom antireflective coating (BARC) thereon (for 248 nm exposure, 60 nm of AR™ 9 antireflective, Rohm and Haas Electronic Materials LLC; or 25 nm an organic underlayer for EUV), and soft baked at 120° C. for 60 seconds (for DUV exposure) or 130° C. for 60 seconds (for EUV exposure), to form a resist film having a thickness of about 50 nm (for DUV exposure) or 60 nm (for EUV exposure). The photoresist layer was exposed through a photomask using a KrF excimer laser (Canon) operating at 248 nm, or using EUV radiation (eMET) operating at 13.4-13.5 nm, and the exposed layers were post-exposure baked (PEB) at 90° C. for 60 seconds. The coated wafers were next treated with a metal ion-free base developer (CD-26 Developer from Rohm and Haas; 0.26 N aqueous tetramethylammonium hydroxide solution) for 60 seconds (DUV exposure) or 30 seconds (EUV exposure) to develop the photoresist layer. The dose-to-clear value ($E_0$) obtained for DUV exposure was 2.7 mJ/cm$^2$, and for EUV exposure was 3.6 mJ/cm$^2$.

Figure 3:
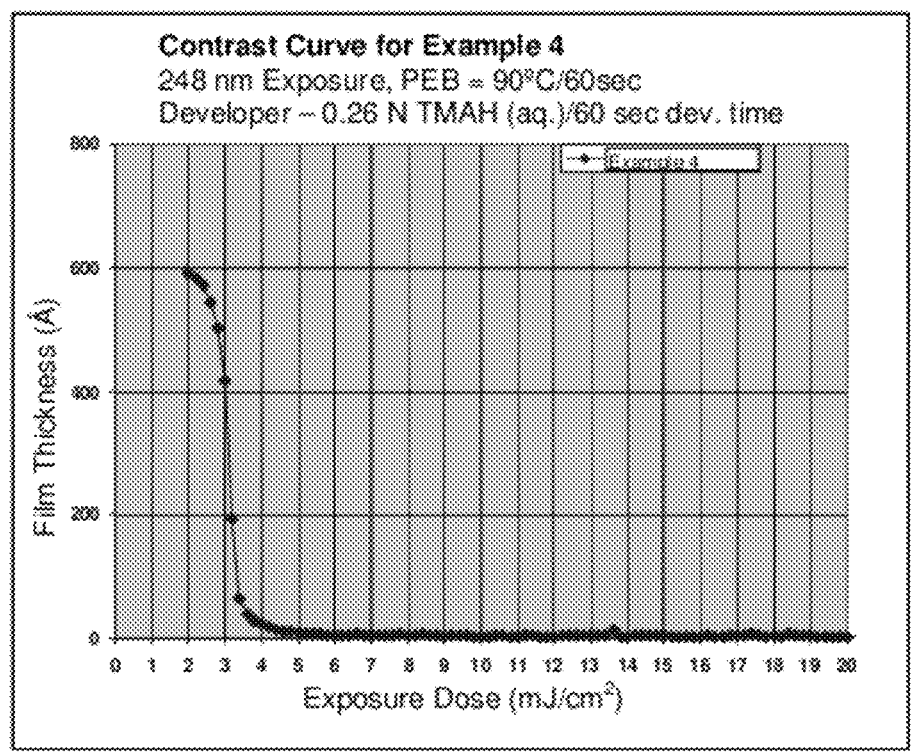
FIG. 3 is a deep ultraviolet (DUV) lithography contrast curve as a plot of feature size (in Angstroms) versus exposure dose (in millijoules per square centimeter, $mJ/cm^2$) for a polymer prepared using an exemplary photoacid generator monomer.

FIG. 3 shows the DUV contrast curve (plot of film thickness (in Angstroms) versus exposure dose (in mJ/cm$^2$) for the above formulated polymer of Example 4. As seen in the contrast curve, the dose-to-clear ($E_0$) obtained for the polymer is 2.7 mJ/cm$^2$.

All ranges disclosed herein are inclusive of the endpoints, and the endpoints are independently combinable with each other. The suffix "(s)" as used herein is intended to include both the singular and the plural of the term that it modifies, thereby including at least one of that term. "Optional" or "optionally" means that the subsequently described event or circumstance can or cannot occur, and that the description includes instances where the event occurs and instances where it does not. As used herein, "combination" is inclusive of blends, mixtures, alloys, or reaction products. All references are incorporated herein by reference.

The use of the terms "a" and "an" and "the" and similar referents in the context of describing the invention (especially in the context of the following claims) are to be construed to cover both the singular and the plural, unless otherwise indicated herein or clearly contradicted by context. Further, it should further be noted that the terms "first," "second," and the like herein do not denote any order, quantity, or importance, but rather are used to distinguish one element from another.

The invention claimed is:

1. A compound having the formula (VII) or (VIII):

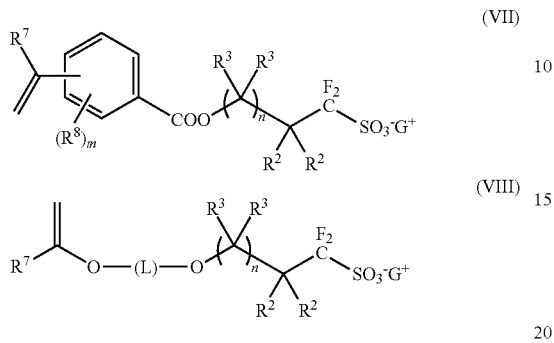

wherein each $R^2$, $R^3$, and $R^7$ is independently H, F, $C_{1-10}$ alkyl, or fluoro-substituted $C_{1-10}$ alkyl, each $R^8$ is independently F, $C_{1-10}$ alkyl, or fluoro-substituted $C_{1-10}$ alkyl, L is a halogenated or non-halogenated $C_{1-30}$ alkylene group, $C_{2-30}$ alkenylene group, monocyclic or polycyclic $C_{3-30}$ cycloalkylene group, monocyclic or polycyclic $C_{6-30}$ arylene group, or monocyclic or polycyclic $C_{7-30}$ alkylene-arylene group, m is an integer of 0 to 4,
n is 1, 2, or 3, and
$G^+$ is an organic or inorganic cation.

2. The compound of claim 1, having the formula:

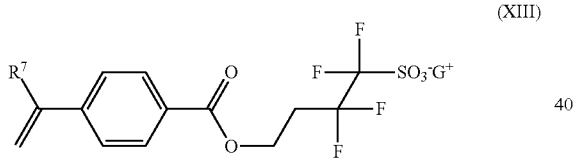

wherein $R^7$ is H, F, $C_{1-10}$ alkyl, or fluoro-substituted $C_{1-10}$ alkyl, and $G^+$ is an organic or inorganic cation.

3. The compound of claim 1, wherein $G^+$ is an alkali metal cation, an alkaline earth metal cation, a main group metal cation, a transition metal cation, an ammonium ion, an alkylammonium ion, an iminium ion, a guanidinium ion, an alkylphosphonium ion, an onium cation of sulfur or iodine, or a combination comprising at least one of the foregoing.

4. The compound of claim 1, wherein $G^+$ is a cation having formula (XIV):

wherein in formula (XIV),
X is S or I,
each $R^0$ is independently a halogenated or non-halogenated group comprising a $C_{1-30}$ alkyl group; a polycyclic or monocyclic $C_{3-30}$ cycloalkyl group; a polycyclic or monocyclic $C_{6-30}$ aryl group; or a combination comprising at least one of the foregoing,
optionally two $R^0$ groups are further attached to one another by a single bond where each $R^0$ group is independently a monocyclic $C_{6-30}$ aryl group, and
a is 2 or 3, wherein when X is I, a is 2, or when X is S, a is 3.

5. The compound of claim 1, wherein G has the formula:

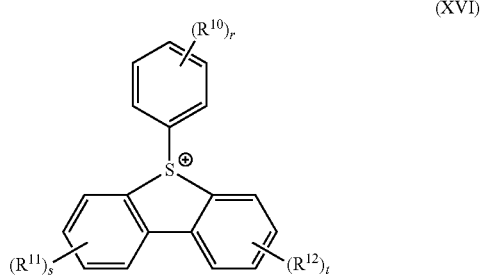

wherein $R^{10}$, $R^{11}$, and $R^{12}$ are each independently hydroxy, halogen, $C_{1-10}$ alkyl, $C_{1-10}$ fluoroalkyl, $C_{1-10}$ alkoxy, $C_{1-10}$ fluoroalkoxy, $C_{6-20}$ aryl, $C_{6-20}$ fluoroaryl, $C_{6-20}$ aryloxy, or $C_{6-20}$ fluoroaryloxy,
r is an integer from 0 to 5; and
s and t are each independently an integer from 0 to 4.

6. A polymer comprising the compound of claim 1.

* * * * *